United States Patent [19]

Mukai

[11] Patent Number: 6,117,129

[45] Date of Patent: Sep. 12, 2000

[54] LASER TREATMENT APPARATUS

[75] Inventor: Hideo Mukai, Toyohashi, Japan

[73] Assignee: Nidek Co., Ltd., Japan

[21] Appl. No.: 09/085,107

[22] Filed: May 28, 1998

[30] Foreign Application Priority Data

| May 30, 1997 | [JP] | Japan | .................................. 9-157692 |
| May 30, 1997 | [JP] | Japan | .................................. 9-157693 |
| Sep. 30, 1997 | [JP] | Japan | .................................. 9-284679 |

[51] Int. Cl.$^7$ .................................................. A61B 18/18
[52] U.S. Cl. .................................. 606/10; 606/17; 606/19
[58] Field of Search .................................. 606/1, 10, 11, 606/12, 14, 15, 16, 17, 19

[56] References Cited

U.S. PATENT DOCUMENTS

| 4,735,603 | 4/1988 | Goodson et al. | ........................ 606/10 |
| 5,200,604 | 4/1993 | Rudko et al. . | |
| 5,474,549 | 12/1995 | Ortiz et al. | ................................ 606/17 |
| 5,575,789 | 11/1996 | Bell et al. . | |
| 5,618,285 | 4/1997 | Zair . | |
| 5,743,902 | 4/1998 | Trost | ........................................ 606/11 |
| 5,797,901 | 8/1998 | Cosmescu | ................................ 606/10 |
| 5,836,909 | 11/1998 | Cosmescu | ................................ 606/15 |
| 5,860,967 | 1/1999 | Zavislan et al. | ............................. 606/9 |
| 5,860,968 | 1/1999 | Wojcik et al. | .............................. 606/16 |
| 5,908,417 | 6/1999 | Miller et al. | ................................. 606/9 |
| 5,941,873 | 8/1999 | Korenfeld | .................................... 606/1 |
| 5,951,544 | 9/1999 | Konwitz | ..................................... 606/17 |
| 5,957,915 | 9/1999 | Trost | ........................................ 606/11 |

FOREIGN PATENT DOCUMENTS

| 0 473 987 | 3/1992 | European Pat. Off. . |
| WO 87/06478 | 11/1987 | WIPO . |
| WO 92/07291 | 4/1992 | WIPO . |

OTHER PUBLICATIONS

Partial European Search Report dated Sep. 11, 1998 (3 pages).
Communication dated Sep. 28, 1998 (1 page).

*Primary Examiner*—Michael Peffley
*Attorney, Agent, or Firm*—Finnegan, Henderson, Farabow, Garrett & Dunner, L.L.P.

[57] ABSTRACT

A laser treatment apparatus has a hand-piece unit with a laser scanner which deflects a laser beam emitted from a laser source to scan a treatment portion of a patient's skin. In the laser treatment apparatus, the first control device controls the laser scanner to perform a laser scanning irradiation. The detection device detects whether the hand-piece unit is electrically connected with the first control device. When the detection device detects the electrical disconnection of the hand-piece unit to the first control device, the second control device forbids the first control device to conduct the laser scanning irradiation.

15 Claims, 6 Drawing Sheets

LASER TREATMENT APPARATUS

BACKGROUND OF THE INVENTION

1. Field of the Invention

The present invention relates to a laser treatment apparatus for treating a patient by irradiating a laser beam to a portion of body to be treated (diseased portion).

2. Description of Related Art

Laser treatment apparatus have been used for the treatment of various diseases based on the selection of the wavelength of treating laser. In the recent neoplasty for removing wrinkles, ephelides, birthmarks, stains, etc. of patients, attention is paid to laser treatment apparatus that use the CO2 laser (carbon dioxide gas laser) having infrared wavelengths. In the neoplasty using these laser treatment apparatus, a hand-piece is used to apply a laser beam emitted from a laser source of the apparatus to a diseased portion. The hand-piece is provided, at its bottom, with one projecting member extending downward and is supported in contact with a patient's body (skin) to surely set a laser irradiation position onto the diseased portion during operation. The laser irradiation onto a remarkably wide area is made with the hand-piece unit provided with a laser scanning device for making a treatment laser beam scan the diseased portion.

However, the hand-piece supported on a patient's body by the one projecting member is in an unstable state and therefore tends to incline. In addition, since the contact area of the projecting member to the patient's body (skin) is extremely small, even a little pressing force by an operator who holds the hand-piece will deform the patient's skin. This deformation of the skin may cause the change in an irradiation distance from a laser emission port to the diseased portion. In particular, in the laser treatment apparatus based on the scanning irradiation of a treatment laser beam, the change in an irradiation distance prevents the precise laser irradiation on the diseased part to be treated.

Furthermore, signals representative of the information relating to a scanning position of a laser beam are constantly transmitted between the hand-piece unit provided with the laser scanning device and a control system through a connector and the like. If this hand-piece unit adapted for a laser scan mode is replaced with a different one for a laser non-scan mode (a laser stationary mode), no signal is transmitted from the hand-piece unit to the control system. In this regard, there is a possibility that the control system detects in error that the laser scanning device of the hand-piece unit is out of order and controls wrong the entire apparatus so as not to operate when a scan made is selected.

On the other hand, the apparatus designed to be operable even when the connector for the hand piece-unit is disconnected may cause a possibility that a laser beam is continuously emitted without scanning to the diseased portion if a scan mode is selected in error.

In neoplasty using the above laser treatment apparatus, when the tissue of the diseased portion is burned by laser irradiation, smoke is generated from the burned diseased portion. The smoke tends to become stains such as soot which will stick to an optical system arranged in a laser emission port, resulting in a decreased power of the laser beam. In addition, the smoke makes it difficult for an operator to observe the diseased portion to be treated by laser irradiation. For a measure to solve the problems, there is known a method of jetting air from the vicinity of the laser emission port of the hand-piece to the diseased portion to eliminate the smoke generated from the diseased portion burned by the laser beam. In this case, an air pump, a gas supply device, arranged independently from the main body of the laser treatment apparatus, is used.

However, the independent air pump must be operated with an extra switch provided separately from a switch for the main body of the laser treatment apparatus, which is troublesome for an operator. In particular, if the operator has to move from his position where he operates the apparatus especially to turning on/off the air pump switch, it imposes a more troublesome work on the operator. Furthermore, the turning on/off of the air pump is left in the operator's hands. If the operator forgets to turn on the switch to activate the air pump at the time of performing laser irradiation, accordingly, the stains resulted from the smoke will stick to the optical system arranged in the laser emission port of the hand-piece, preventing good observations of the diseased portion. The air pump disposed independently from the main body of the laser treatment apparatus requires a large installation space for the whole apparatus.

SUMMARY OF THE INVENTION

The present invention has been made in view of the above circumstances and has an object to overcome the above problems and to provide a laser treatment apparatus capable of providing a stable irradiation distance from a laser emission port to a portion to be treated, easily holding a hand-piece in a stable state, and identifying the hand-piece for laser scan even if the hand-piece is replaced with one of other different types of hand-pieces to prevent the malfunctioning of the apparatus due to a replacement of the hand-pieces.

Another object of the present invention is providing a laser treatment apparatus capable of reducing an installation space of the whole apparatus and facilitating the operation for activating an air pump to prevent an operator from forgetting to activate the air pump.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, according to the present invention, there is provided a laser treatment apparatus comprising a hand-piece unit provided with a laser beam scanning means which deflects a laser beam emitted from a laser source to scan a portion to be treated, the apparatus comprising first control means for controlling the laser beam scanning means to deflect the laser beam to scan, detection means for detecting whether the hand-piece unit is electrically connected to the first control means, and second control means for forbidding the first control means to deflect the laser beam to scan when the detection means detects electrical disconnection of the hand-piece unit to the first control means.

According to a second aspect of the present invention, there is provided a laser treatment apparatus for performing laser beam irradiation on a portion to be treated with a laser beam emitted from a treatment laser source, the apparatus comprising a multi-jointed arm for introducing the laser beam to a predetermined position, and a hand-piece unit provided with two or more contact portions arranged so as to be put at substantially even intervals on a periphery of the treatment portion and at least a part having a visible light transmittance property to enable an operator to view the irradiation area, the hand-piece unit being detachably connected to the multi-jointed arm section.

According to a third aspect of the present invention, there is provided a laser treatment apparatus comprising a hand-piece with a laser emission port and means for introducing a laser beam from a treatment laser source to the laser emission port of the hand-piece, which irradiates the laser beam emitted through the laser emission port to a portion to be treated, the apparatus comprising gas supply means for feeding gas to eliminate smoke generated from the treatment portion irradiated by the laser beam, gas jetting means for jetting the gas fed from the gas supply means and introduced to the hand-piece to a vicinity of the laser emission port, first signal generation means for generating a signal for driving a laser unit of the laser treatment apparatus, second signal generation means for generating a signal for driving the laser source, wherein the gas supply means operates interlocking with the signal generated in the first or second signal generating means.

In the above apparatus according to the present invention, a stable irradiation distance can be provided between the laser emission end port and the treatment portion, causing no malfunctioning of the apparatus due to a replacement of hand-pieces.

Furthermore, the operability to activate the gas supply means can be improved, ensuring elimination of the smoke generated due to the laser irradiation and to prevent stains resulted from the smoke with respect to the laser scanning means of the hand-piece unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of a laser treatment apparatus embodying the present invention will now be given referring to the accompanying drawings.

Figure 1:
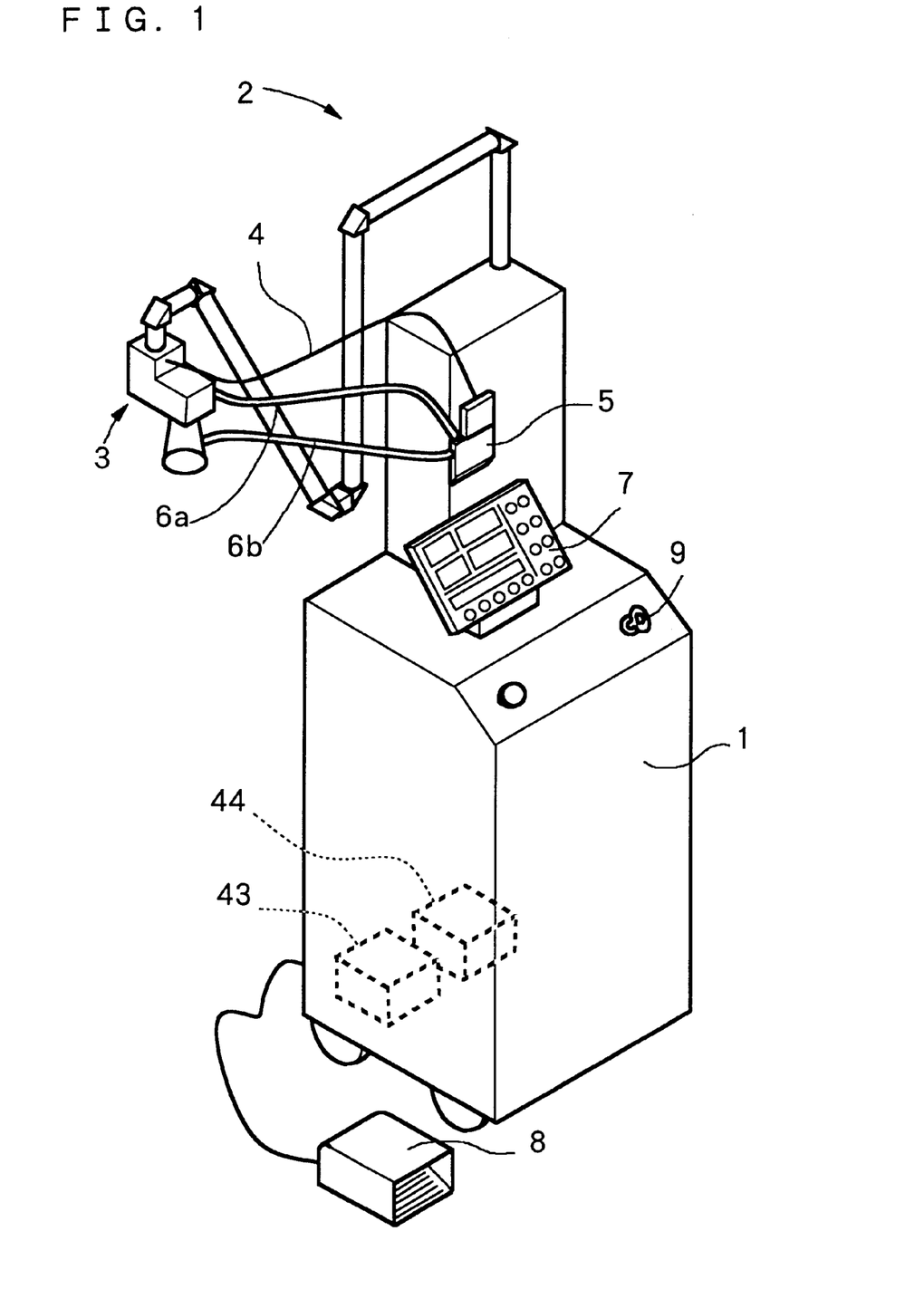
FIG. 1 is a schematic perspective view of a laser treatment apparatus in an embodiment according to the present invention.

FIG. 1 is a schematic perspective view of the laser treatment apparatus in the embodiment.

As shown in FIG. 1, the laser treatment apparatus is provided with a laser unit 1, a multi-jointed arm 2, a hand-piece unit 3 having a laser emission port, a cable 4, a connector 5, air tubes 6a and 6b, a control panel 7 which is used by the operator to set laser irradiation conditions, etc., and a foot switch 8 which is depressed by the operator to produce a trigger signal whereby to emit a laser beam. The connector 5 is provided with a microswitch 42 for detecting the connection or disconnection of the cable 4. Also, a key switch 9 for turning on/off the power to the laser unit 1 is provided on a front part of the laser unit 1.

The laser unit 1 further includes an air purge pump 43, a smoke evacuator 44, a controller 40 which will be described later, a laser source 31 for emitting a treatment laser beam, an aiming light source 32, and others. The air purge pump 43 and the smoke evacuator 44 are installed in the laser unit 1 with rubber attachment members whereby to prevent the vibration caused by the activation of the air purge pump 43 and the smoke evacuator 44 from being transmitted to the whole apparatus. The installation of the air purge pump 43 and the smoke evacuator 44 in the laser unit 1 needs not an extra installation space for them, and also the cables connecting the air purge pump 43 and the smoke evacuator 44 to the controller 40 do not become obstacles to an operator. In this embodiment, the treatment laser source 31 is a $CO_2$ laser source that emits an infrared laser beam, and the aiming light source is a semiconductor laser that emits a visible red laser beam.

The multi-jointed arm 2 is made up of several rigid pipes movably linked by joints, so that the operator can move freely the hand-piece unit 3 which is attached at the end of the arm 2. Mirrors are fitted in the joints of the multi-joint arm 2 so that the treatment laser beam and aiming light beam that are aligned coaxially with each other in the laser unit 1 are guided to pass through the multi-jointed arm 2 and reach the hand-piece unit 3. The hand-piece unit 3 is among a variety of detachable units designed to meet individual purposed and usage. For the following explanation of this embodiment, the apparatus is equipped with a scanning hand-piece unit 3 provided with a scanner head which deflects the laser beam to scan the treatment portion of a patient.

Figure 2:
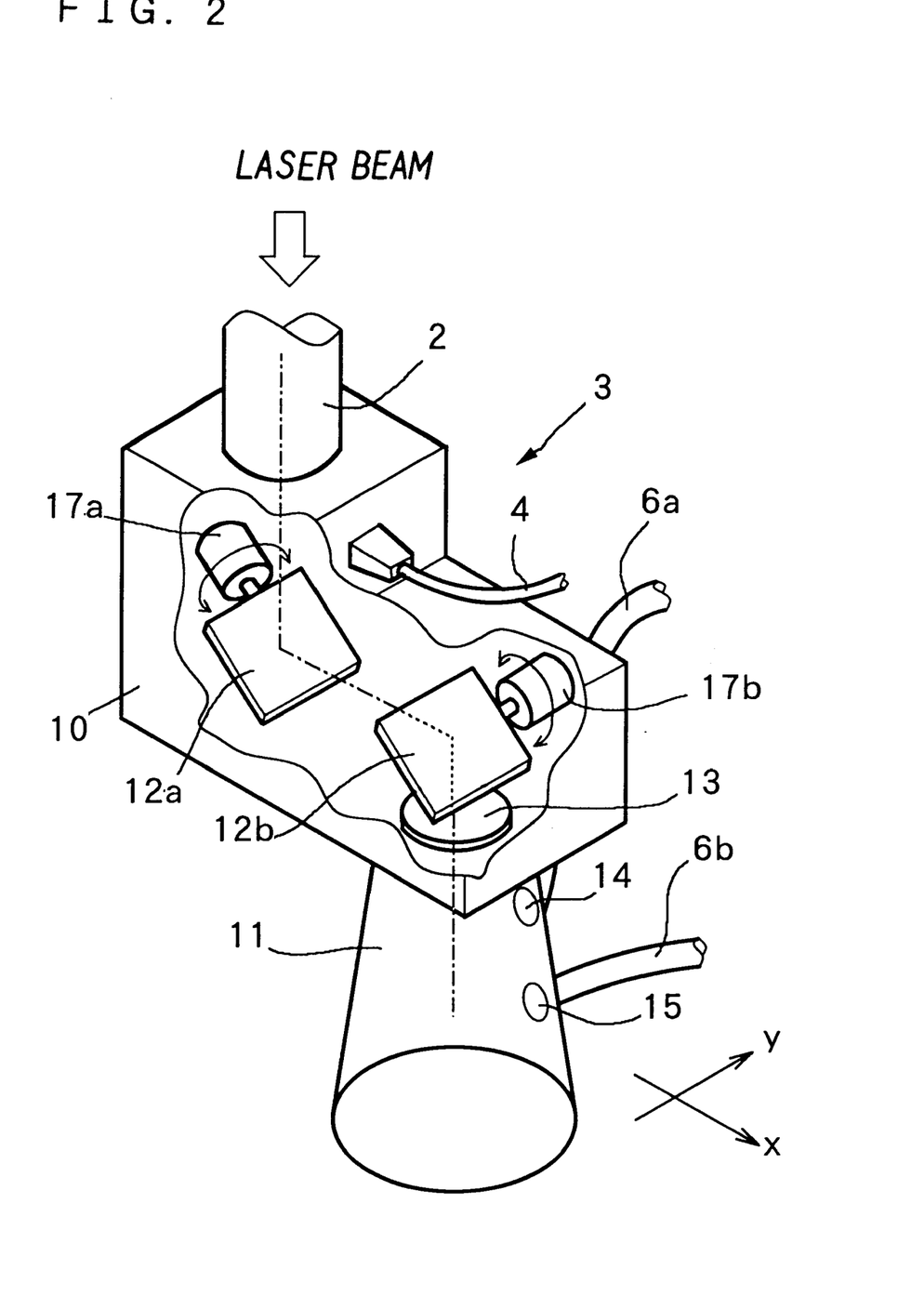
FIG. 2 is an explanatory view of a hand-piece unit of the apparatus.

FIG. 2 is an explanatory view of a hand-piece unit of the laser treatment apparatus. The hand-piece unit 3 consists of a scanner 10 and a hand-piece head 11 which are separable. The scanner 10 incorporates driven mirrors 12a and 12b which deflect the treatment laser beam and aiming light beam, which have come through the multi-joint arm 2, to scan the treatment portion in the X/Y directions, drive motors 17a and 17b which swing the mirrors 12a and 12b, and a focusing lens 13.

The drive motors 17a and 17b are controlled by a scanner controller 41 provided in the laser unit 1. The controller 40 produces drive currents, which are fed through the connector 5 and cable 4 to the drive motors 17a and 17b in the scanner 10, by which the driven mirrors 12a and 12b are swung.

The hand-piece head 11 is made of transparent resin, having a generally cone shape to cover the laser scanning area at its bottom, so that the operator can view from outside the treating area and irradiation area covered by the hand-piece head 11. The hand-piece head 11 has in its side wall the formation of an air jet port 14 through which air is introduced to prevent stains caused by the smoke generated from the treating area during laser irradiation from being stuck to the optical system including the condensing lens 13 arranged at the laser emission port, a smoke outlet 15 which clears the treating area of smoke produced by the laser irradiation. In operation, a jet of air produced by the air purge pump 43 in the laser unit 1 is conducted through the air tube 6*a* to the air jet port 14 located near the top of the hand-piece head 11. An evacuation of smoke, on the other hand, is conducted by the smoke evacuator 44 in the laser unit 1, which sucks the smoke through the air tube 6*b*.

Incidentally, the bottom of hand-piece head 11 has the size which can secure the scanning area of the laser beam for the treatment.

Figure 3:
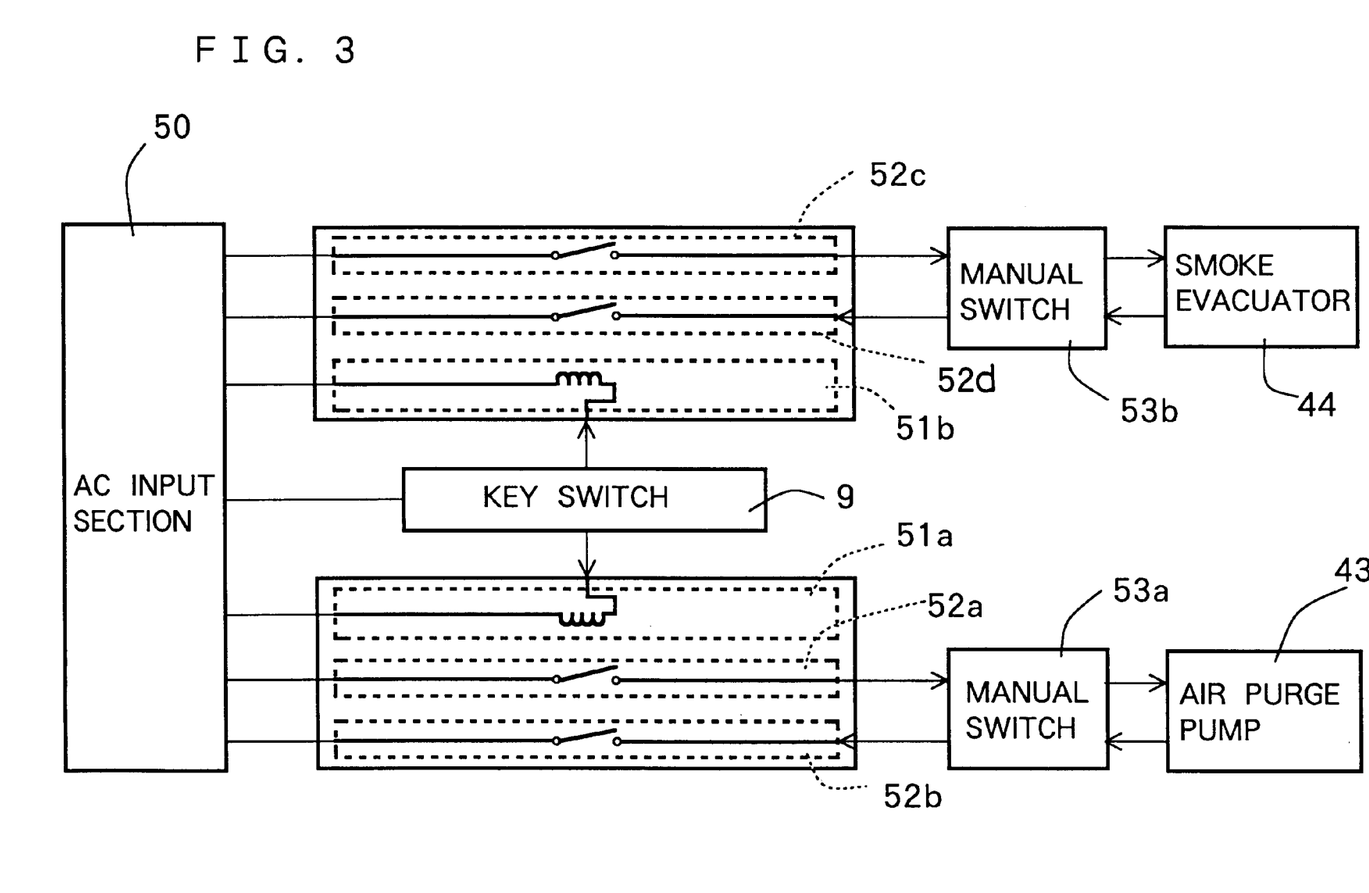
FIG. 3 is a block diagram of an electric system to activate an air purge pump and a smoke evacuator.
Figure 4:
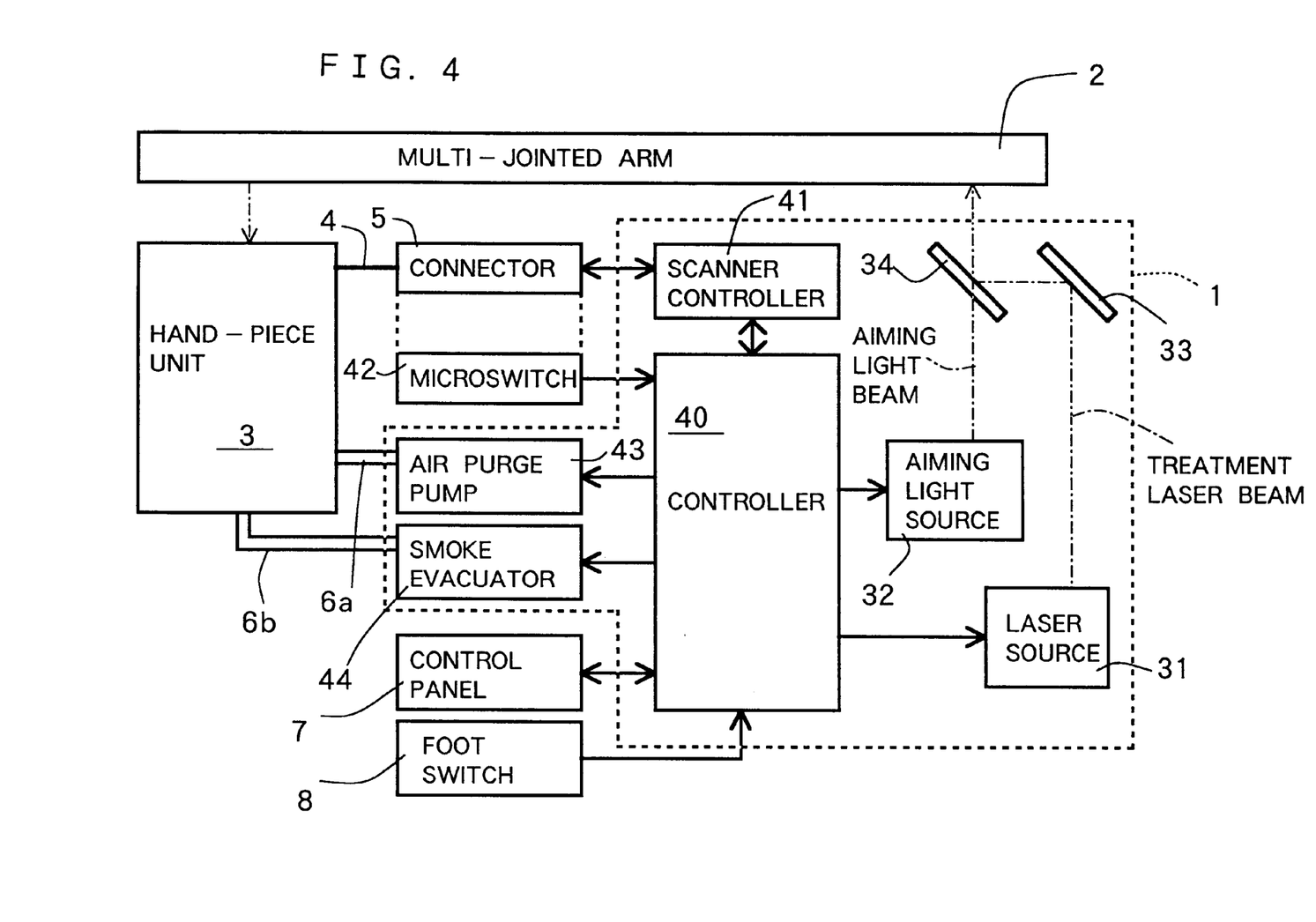
FIG. 4 is a block diagram of a basic overall arrangement and the control system of the laser treatment apparatus in the embodiment.

The operation of the apparatus constructed as above will be described below, referring to FIGS. 3 and 4. FIG. 3 is a block diagram of an electric system to activate an air purge pump 43 and a smoke evacuator 44. FIG. 4 is a block diagram of a main structure including a control system of the laser treatment apparatus.

When the key switch 9 is turned on to actuate the laser unit 1, an AC input section 50 produces a current to power relays 51*a* and 51*b*. On receiving the current, the power relays 51*a* and 51*b* generate a magnetic field with magnetic power to turn on switches 52*a* and 52*b* for the air purge pump 43 and switches 52*c* and 52*d* for the smoke evacuator 44 respectively. The pump switches 52*a* and 52*b* and the evacuator switches 52*c* and 52*d* turned on allow the current to flow in the air purge pump 43 and the smoke evacuator 44, thereby activating them. The air supplied from the air purge pump 43 is fed to the hand-piece unit 3 through the air tube 6*a* and jetted through the air jet port 14 of the hand-piece head 11. On the other hand, the air in the head 11 is sucked by the smoke evacuator 44 through the smoke outlet 15 and the air tube 6*b*. As shown in FIG. 3, a manual switch 53*a* for pump and a manual switch 53*b* for evacuator are provided. They are connected with contact points at an initial state where the key switch 9 is turned on.

In the above embodiment, two switches are provided for each of the air purge pump 43 and the smoke evacuator 44 because even if one of the switches is broken down and thus continuously kept as turned on, another switch can be turned off by turning off the key switch 9 to surely stop the operation of the air purge pump 43 and the smoke evacuator 44. However, those switches may be one each for the pump and the evacuator.

Turning on the key switch 9 causes the current to flow in each section of the apparatus, the apparatus implements a self-check and displays a message of "self-check state" in a display on the control panel 7. Upon completion of the check for each section, the control unit 40 automatically enters the standby state, causing the control panel 7 to display a message of "standby state" thereon.

In the self-check (or during the power-on period), the controller 40 checks the connection of the cable 4 to the connector 5 by means of a microswitch 42. If disconnection is detected, the controller 40 cuts off the power supply to the scanner controller 41, thereby preventing the malfunctioning of the apparatus.

The operator confirms the apparatus in a standby state by viewing the display on the control panel 7, and brings the entire bottom plane of the hand-piece unit 3 in contact with the patient's body so as to cover the treatment portion. In the case of the treatment by scanning treatment laser, the operator depresses in advance a key on the control panel 7 to select a scan mode of an irradiation mode. From the hand-piece unit 3, the aiming light beam emitted from the aiming light source 32 is irradiated to the treating area. While observing the irradiation position by the aiming light, the operator selects irradiation conditions, for example, an irradiation pattern, the shape of an irradiation area, the size of same, with the keys on the control panel 7, and make a fine adjustment of the irradiation position with an alignment key.

At this time, since the hand-piece head 11 is made of transparent resin, the operator can easily observe the irradiation position and the irradiation area and the like even if the treatment portion is covered by the hand-piece head 11 with its bottom brought into contact with the patient's body. The hand-piece head 11 being formed into a substantially cone, its bottom comes into contact almost uniformly with the patient's body. Accordingly, the distance from the laser emission port or end of the scanner 10 to the treating area can be kept stably, and the operator can easily hold the hand-piece unit 3 in that state. The head 11 is in contact with the patient's body, skin, in a relatively large contact area, dispersing the force of pressing the skin, which prevents the peripheral portion of the treating area from easily deforming. This makes it possible to provide a constant stable irradiation distance.

After the setting of the irradiation conditions and the determination of the area to be irradiated based on the observation of the aiming light beam, the operator pushes a READY/STANDBY key on the control panel 7 so that the apparatus turns to a ready state. Then, the operator depresses the foot switch 8 to generate a trigger signal. The controller 40 which has received the trigger signal operates on the laser source 31 to emit a treatment laser beam in accordance with the setting irradiation conditions.

The treatment laser beam emitted from the laser source 31 is reflected by a mirror 33 and the a dichroic mirror 34, aligned coaxially to the aiming light beam emitted from the aiming light source 32, and introduced to the multi-jointed arm 2. The coaxial treatment laser beam and aiming light beam are reflected by the mirrors disposed at the joints of the arm 2 and led to the hand-piece unit 3. The scanner controller 41 operates on the driving motors 17*a* and 17*b* in accordance with the setup signals of the form and size of irradiation area. In this way, the treatment laser beam is deflected to scan the diseased portion.

When the scanning hand-piece unit 3 is used, signals are constantly transmitted-received between the scanner controller 41 and the hand-piece unit 3 through the connector 5. When no feed back signal is returned from the hand-piece unit 3 to the scanner controller 41, an error message is displayed. When the cable 4 is merely disconnected with the connector 5, the controller 40 cuts off the power supply to the scanner controller 41 based on the detection signal from the microswitch 42 and causes the control panel 7 to display the message informing that the laser scanning hand-piece unit 3 is not connected to the laser unit 1. Accordingly, the operator can confirm whether the apparatus is in the connection error between the scanner controller 41 and the hand-piece unit 3 or the only disconnection of the cable 4 to the connector 5, and take an appropriate measure.

A hand-piece unit different from the laser scanning hand-piece unit 3 needs no operation of the scanner controller 41. The controller 40 therefore cuts off the power supply to the scanner controller 41 in accordance with the information on the connection state of the cable 4 to the connector 5, so that the apparatus does not enter a scan mode even if the operator select in mistake the scan mode, thereby preventing the malfunctioning of the apparatus.

During laser irradiation, though the smoke is generated from the irradiated portion, the air is jetted thereto through the air jet port 14 of the hand-piece head 11 and the smoke is sucked through the smoke outlet 15, thereby eliminating the smoke generated at the irradiated portion outward the head 11. Since the air purge pump 43 and the smoke evacuator 44 have been activated at the time of input of the key switch 9 which is turned on to activate the apparatus, the operator has not to additionally operate any switch to eliminate the smoke and can perform a laser irradiation operation on the diseased portion while observing it. It is also possible to prevent stains caused by the smoke from being stuck to the optical system provided in the vicinity of the laser emission port of the hand-piece head 11.

If not needed, the air supply may be stopped with the manual switch 53a and the smoke evacuation (the air suction) may be stopped with the manual switch 53b, respectively. These manual switches 53a and 53b may be either a common switch for the air supply and the smoke evacuation or separate switches.

When the key switch 9 is turned off to cut off the power supply to the laser unit 1 after completion of the laser treatment, the pump switches 52a and 52b and the evacuator switches 52c and 52d become off, thus stopping the air purge pump 43 and the smoke evacuator 44.

In the above embodiment, the air purge pump 43 and the smoke evacuator 44 are activated interlocking with the ON/OFF state of the key switch 9; however, they may be operated interlocking with the input of other keys, for example, the READY/STANDBY key.

Figure 5:
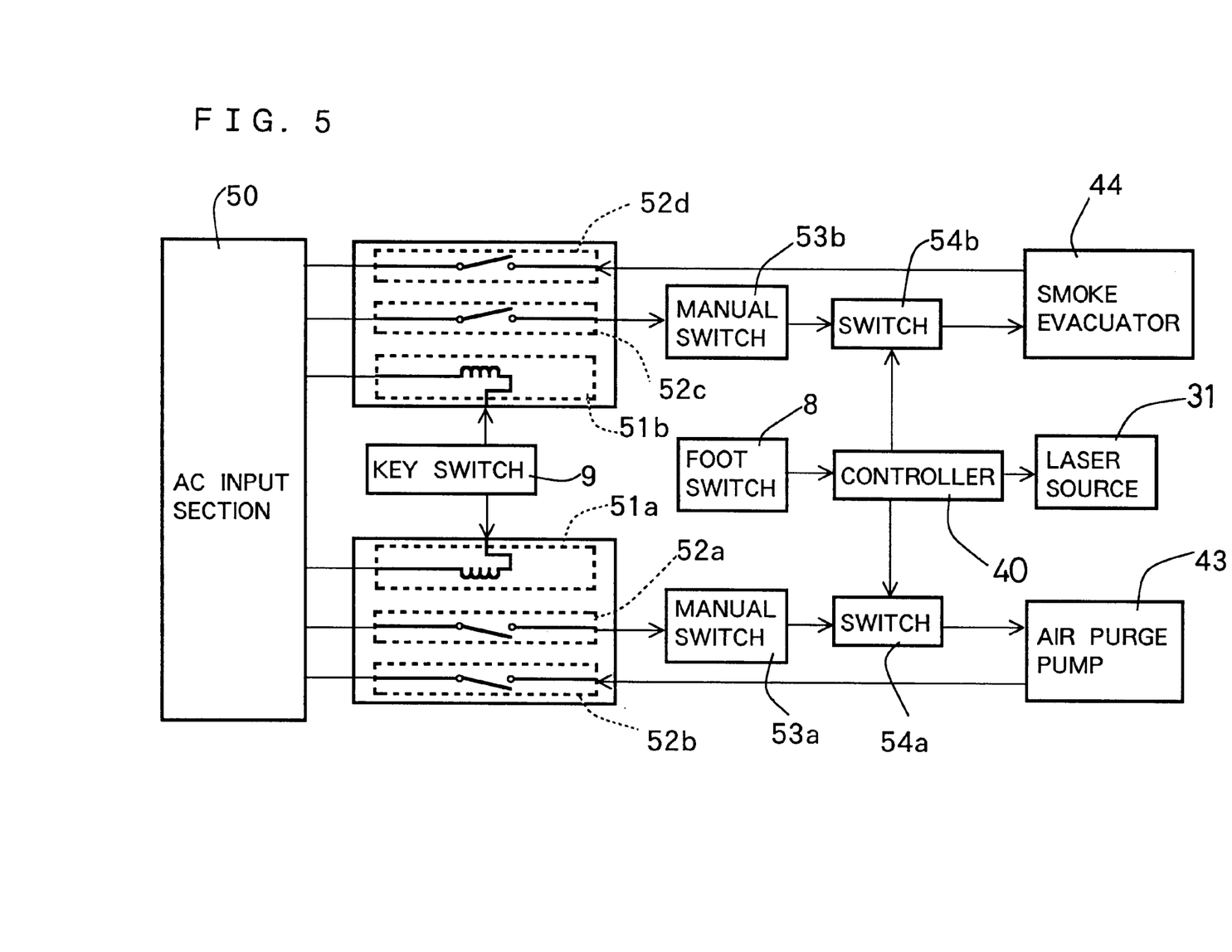
FIG. 5 is a block diagram of an electric system to activate the air purge pump and the smoke evacuator in response to input signals from a foot switch.

Also, the air purge pump 43 and the smoke evacuator 44 may be activated in response to the input signal from the foot switch 8 depressed for performing laser irradiation. The operation in this case will be described with reference to an electric system shown in FIG. 5, wherein the same structures as in FIGS. 3 and 4 are provided with the same numbers. Turning on the key switch 9 makes the pump switches 52a and 52b and the evacuator switches 52c and 52d become ON, while a switch 54a disposed between the manual switch 53a and the air purge pump 43 and another switch 54b disposed between the manual switch 53b and the smoke evacuator 44 are in an OFF state. At this state, the air purge pump 43 and the smoke evacuator 44 are at rest. When the foot switch 8 is depressed after completion of the preparation for laser irradiation, a trigger signal is input to the controller 40, thereby causing the laser source 31 to emit a treatment laser beam. The controller 40 keeps the switches 54a and 54b turning ON during actuation of the laser source 31 and continuously a predetermined time α. Consequently, the air purge pump 43 and the smoke evacuator 44 are activated during the laser irradiation to jet and suck air from the hand-piece unit 3 in order to eliminate the smoke generated from the laser irradiated portion of the skin. The air purge pump 43 and the smoke evacuator 44 are operated continuously for the predetermined time α after completion of the laser irradiation, thereby fully eliminating the smoke generated from the laser irradiated portion for a while after completion of the laser irradiation. The air purge pump 43 may be interlocked with the ON/OFF state of the key switch 9 and the smoke evacuator 44 may be interlocked with the input signal from the foot switch 8.

An input device may be provided in the control panel 7 or the laser unit 1 of the apparatus, whereby to optionally set an air supply amount per hour from the air purge pump 43. With the input device, the controller 40 may operate the air purge pump 43 so as to regulate the air supply amount. This makes it possible to supply air of an appropriate amount even when an amount of the smoke generated changes depending on treatment conditions and cases. Similarly, it may be constructed so as to optionally set an air suction (elimination) amount per hour by the smoke evacuator 44.

The present invention may be embodied in other specific forms without departing from the spirit or essential characteristics thereof.

Figure 6:
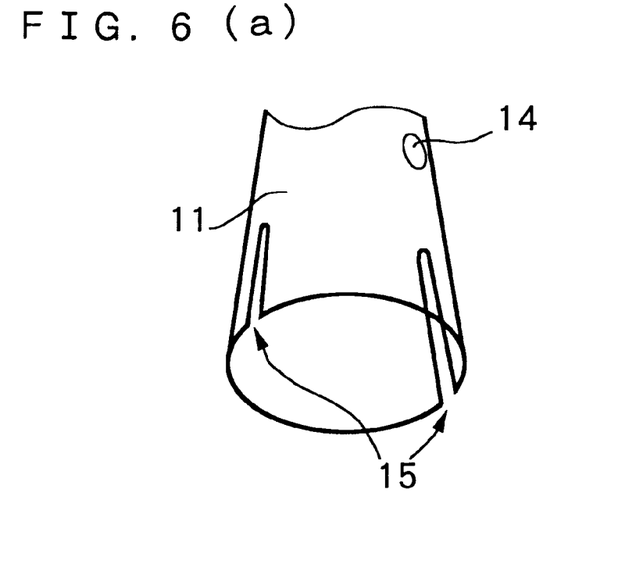
FIG. 6(a) is a perspective view of a variation of a hand-piece head of the hand-piece unit.
FIG. 6(b) is a perspective view of another variation of a hand-piece head of the hand-piece unit.

For instance, the apparatus may be designed such that the smoke evacuator 44 and the air tube 6b are omitted and the air jetting through the air jet port 14 from the air purge pump 43 makes the smoke be discharged outside through the smoke outlet 15. In this case, the smoke outlet 15 is preferably formed into plural cut portions as shown in FIG. 6(a).

If the hand-piece head 11 is designed so that its bottom come into contact with the periphery of an diseased portion in at least three points, an operator can hold the hand-piece unit 3 in a stable state. In the above case of omitting the smoke evacuator 44, the smoke outlet 15 may be omitted if the head 11 is provided with long contact portions as shown in FIG. 6(b).

As mentioned above, the present invention can provide and keep a stable irradiation distance from the laser emission end port to the diseased portion, preventing the malfunctioning of the apparatus due to a replacement of hand-pieces.

According to the present invention, furthermore, an installation space of the whole apparatus can be reduced and the operability to activate the air pump can be improved, preventing the operator from forgetting the activation of the air pump. It is therefore possible to eliminate the smoke generated due to the laser irradiation and to prevent stains due to the smoke from sticking to the optical system disposed in the vicinity of the laser emission port.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A laser treatment apparatus comprising a hand-piece unit provided with a laser beam scanning means which deflects a laser beam emitted from a laser source to scan a portion of a body of a patient to be treated, the apparatus comprising:

first control means for controlling said laser beam scanning means to deflect the laser beam to scan;

detection means for detecting whether said hand-piece unit is electrically connected to said first control means; and     second control means for forbidding said first control means to deflect the laser beam to scan when said detection means detects an electrical disconnection of said hand-piece unit to said first control means, wherein said hand-piece unit is connected with said first control means through a connector and a cable, and said detecting means detects connection of said hand-piece unit to the connector.

2. A laser treatment apparatus according to claim 1 further comprising selection means for selecting one of a laser scan mode in which laser scanning irradiation takes place and a laser stationary mode in which laser stationary irradiation takes place,     wherein said second control means forbids said selection means to select the laser scan mode when said detecting means detects electrical disconnection of said hand-piece unit to said first control means.

3. A laser treatment apparatus according to claim 1, wherein said hand-piece unit is provided with a hand-piece head having two or more contact portions arranged so as to be put at substantially even intervals on a periphery of the treatment portion whereby to determine an area to be irradiated with a laser beam by the operation of said laser beam scanning means and to keep a predetermined distance from the treatment portion, said hand-piece head having at least a part having a visible light transmittance property to enable an operator to view the irradiation area.

4. A laser treatment apparatus according to claim 3, wherein said hand-piece head has a substantially cone shape.

5. A laser treatment apparatus according to claim 3, wherein said contact portions come into contact with the periphery of the treatment portion in at least three points.

6. A laser treatment apparatus according to claim 3, wherein said hand-piece head comprises:

a jet port through which gas fed from a gas supply device is jetted to a vicinity of a laser emission port to eliminate smoke generated from the treatment portion irradiated by the laser beam; and a smoke outlet through which the smoke generated from the treatment portion is evacuated.

7. A laser treatment apparatus according to claim 6, wherein said smoke outlet is connected to a smoke evacuation device to evacuate the smoke.

8. A laser treatment apparatus according to claim 1, further comprising:

gas supply means for feeding gas for eliminating smoke generated from the treatment portion irradiated by the laser beam;

gas jetting means for jetting the gas fed from said gas supply means to a vicinity of a laser emission port of said hand-piece unit;

first signal generation means for generating a signal for driving a laser unit of said laser treatment apparatus;

second signal generation means for generating a signal for driving the laser source;

wherein said gas supply means operates interlocking with the signal from said first or second signal generating means.

9. A laser treatment apparatus according to claim 8, wherein said second signal generating means comprises a foot switch which generates a signal for driving the laser source, and said gas supply means operates in accordance with the signal from said foot switch.

10. A laser treatment apparatus according to claim 9, wherein said gas supply means continuously operates for a predetermined time even after the end of the laser source in accordance with the signal from said foot switch.

11. A laser treatment apparatus according to claim 8, wherein said gas supply means is built in the laser unit of said laser treatment apparatus.

12. A laser treatment apparatus according to claim 8, further comprising smoke evacuation means for evacuating the smoke generated from the treatment portion, which operates interlocking with the signal generated by said first or second signal generating means.

13. A laser treatment apparatus according to claim 12, wherein said second signal generating means comprises a foot switch which generates a signal for driving the laser source, and said smoke evacuation means operates in accordance with the signal from said foot switch.

14. A laser treatment apparatus according to claim 13, wherein said smoke evacuation means continuously operates even after driving of the laser source is stopped in accordance with the signal from said foot switch.

15. A laser treatment apparatus according to claim 12, wherein said smoke evacuation means is built in the laser unit of said laser treatment apparatus.

* * * * *